(12) United States Patent
Katayama et al.

(10) Patent No.: US 8,257,978 B2
(45) Date of Patent: Sep. 4, 2012

(54) METHOD OF EVALUATING REACTION BETWEEN DISSOLVED HYDROGEN AND DISSOLVED OXYGEN AND METHOD OF EVALUATING ABILITY OF DISSOLVED HYDROGEN TO SCAVENGE ACTIVE OXYGEN IN WATER

(75) Inventors: Seiji Katayama, Shizuoka (JP); Yumiko Katayama, Shizuoka (JP)

(73) Assignees: Eureka-Lab Inc., Shizuoka (JP); Seiji Katayama, Shizuoka (JP)

(*) Notice: Subject to any disclaimer, the term of this patent is extended or adjusted under 35 U.S.C. 154(b) by 176 days.

(21) Appl. No.: 12/920,933

(22) PCT Filed: Mar. 4, 2009

(86) PCT No.: PCT/JP2009/054087
§ 371 (c)(1),
(2), (4) Date: Nov. 1, 2010

(87) PCT Pub. No.: WO2009/110515
PCT Pub. Date: Sep. 11, 2009

(65) Prior Publication Data
US 2011/0039348 A1  Feb. 17, 2011

(30) Foreign Application Priority Data
Mar. 4, 2008 (JP) .................................. 2008-054107

(51) Int. Cl.
*G01N 33/00* (2006.01)
*G01N 27/27* (2006.01)

(52) U.S. Cl. ........ 436/138; 436/127; 436/136; 436/144; 436/150; 436/151; 436/182

(58) Field of Classification Search ............... 436/127, 436/136, 138, 144, 150–151, 182
See application file for complete search history.

(56) References Cited

U.S. PATENT DOCUMENTS

| | | | | |
|---|---|---|---|---|
| 4,171,350 A | * | 10/1979 | Sanders ..................... | 423/580.1 |
| 4,211,615 A | * | 7/1980 | Hallberg et al. ............. | 205/786 |
| 4,789,488 A | * | 12/1988 | deSilva ..................... | 210/750 |
| 4,960,497 A | * | 10/1990 | Gallagher .................. | 205/785.5 |
| 2004/0094508 A1 | * | 5/2004 | Nakasaki .................... | 216/63 |
| 2005/0084615 A1 | * | 4/2005 | Weidman et al. ............. | 427/305 |
| 2009/0035383 A1 | * | 2/2009 | Ohta et al. .................. | 424/600 |
| 2010/0291228 A1 | * | 11/2010 | Ohta et al. .................. | 424/600 |
| 2011/0151058 A1 | * | 6/2011 | Yoshida ..................... | 426/67 |

OTHER PUBLICATIONS

Neidrach, L. W. et al, Analytical Chemistry 1982, 54, 1651-1654.*
Chapelle, F. H. et al, Environmental Science and Technology 1996, 30, 3565-3569.*
Li, K. et al, Water Research 2000, 34, 2011-2024.*
Goodisman, J. et al, Journal of Physical Chemistry A 2000, 104, 12029-12044.*
Ryu, J.-H. et al, Environmental Science and Technology 2004, 38, 5950-5957.*

* cited by examiner

*Primary Examiner* — Arlen Soderquist
(74) *Attorney, Agent, or Firm* — Wenderoth, Lind & Ponack, L.L.P.

(57) ABSTRACT

Provided are novel technical means for obtaining useful knowledge in practical application of antioxidation action of dissolved hydrogen and in practical application of active oxygen scavenging action in water.
Based on the temporal profile of the difference between the dissolved oxygen amount measured with forcibly dissolving hydrogen and the dissolved oxygen amount measured with blowing any other gas than hydrogen, the reaction between dissolved hydrogen and dissolved oxygen is quantitatively evaluated. Based on the temporal profile of the difference between the dissolved oxygen amount measured with making a photosensitizing dye contained in water and with forcibly dissolving hydrogen therein, and the dissolved oxygen amount measured without making a photosensitizing dye contained in water and with forcibly dissolving hydrogen therein, the reaction between dissolved hydrogen and dissolved oxygen is quantitatively evaluated.

2 Claims, 11 Drawing Sheets

METHOD OF EVALUATING REACTION BETWEEN DISSOLVED HYDROGEN AND DISSOLVED OXYGEN AND METHOD OF EVALUATING ABILITY OF DISSOLVED HYDROGEN TO SCAVENGE ACTIVE OXYGEN IN WATER

This application is a U.S. national stage of International Application No. PCT/JP2009/054087 filed Mar. 4, 2009.

TECHNICAL FIELD

The present invention relates to an evaluation method for the reaction between dissolved hydrogen and dissolved oxygen and to an evaluation method for the active oxygen scavengeability in water of dissolved hydrogen.

BACKGROUND ART

Hydrogen molecules (atoms) have heretofore been known to have reducibility, and have been put in practical application for reduction reaction (hydrogenation reaction) in chemical synthesis, etc.

However, the matter as to how and by what mechanism the relatively stable hydrogen molecules could exhibit reducibility is in the process of developing studies. It has been presumed that, just before the reaction, hydrogen could be in the active state "atomic hydrogen", or "nascent hydrogen", however, the theoretical rationale for the physical properties is as yet still left unsolved.

For noticeably getting out the reducibility of hydrogen molecules, in general, a metal catalyst or the like has been used for the purpose of lowering the activation energy for reaction. According to the method of using such a metal catalyst, it is said that the hydrogen adsorbed by the metal surface becomes atomic hydrogen and acts for reduction. On the other hand, it is known that, when hydrogen molecules have dissolved in water, they exhibit an extremely high reduction potential, and it is understood that this phenomenon would be based on the same action as above. However, the reducibility character and the stoichiometric nature thereof are as yet left unsolved.

For example, it is known that when hydrogen molecules are dissolved in water, the oxidation-reduction potential therein changes from about 250 mV before the dissolution to about −500 mV after the dissolution. Owing to such a high reduction potential of the dissolved hydrogen water, the dissolved hydrogen water is anticipated to have the function of antioxidation and active oxygen scavengeability, and in particular, since the relation between active oxygen and human health has been reported, many researchers and persons on the street are concerned about this issue.

In fact, we face various realistic evidence that iron rusts in tap water but not in hydrogen water, and green tea does not discolor in brown in hydrogen water; unfortunately, however, we could not reach any inflexible academic verification as yet.

One factor is that active oxygen has an extremely short life. For example, some investigations have been made for capturing the behavior of active oxygen having a short life, according to a method of spectroscopy in a system where the signals are rapid, such as ESR (electron spin resonance) or luminescence measurement; however, it is said that further investigations in novel aspects would be necessary for obtaining detailed knowledge relating to the reaction between dissolved hydrogen in water and active oxygen.

The present inventors have made investigations for the technology of obtaining a reducible hydrogen solution with a large quantity of hydrogen dissolved therein within a short period of time by dispersing hydrogen microbubbles in water or in solution (see Patent Reference 1); and based on the previous knowledge, the inventors have further investigated the relation between dissolved hydrogen and active oxygen in water stoichiometrically and from the viewpoint of capturing the reaction speed in a large volume, thereby exploring a novel method for obtaining useful knowledge in application of dissolved hydrogen to active oxygen scavenging.

[Patent Reference 1] WO2008/156171

DISCLOSURE OF THE INVENTION

Problems that the Invention is to Solve

Accordingly, in the background as above, the present invention is, as its object, to provide a novel technical means for obtaining useful knowledge in practical application of dissolved hydrogen for antioxidation and practical application thereof for active oxygen scavenging reaction in water.

Means for Solving the Problems

To solve the above-mentioned problems, the invention is characterized by the following:

First: A method for evaluating the reaction between dissolved hydrogen and dissolved oxygen, which comprises a step of forcibly reducing the dissolved oxygen amount in water by blowing thereinto any other gas than hydrogen to thereby make the dissolved oxygen amount in water reach a predetermined initial concentration, followed by measuring the temporal dissolved oxygen amount in water, a step of forcibly dissolving hydrogen in water to thereby adjust the dissolved oxygen amount in water to the initial concentration, followed by measuring the temporal dissolved oxygen amount in water, and a step of quantitatively evaluating the reaction between the dissolved hydrogen and the dissolved oxygen based on the time-profile of the difference between the dissolved oxygen amount measured with forcibly dissolving hydrogen and the dissolved oxygen amount measured with blowing the other gas than hydrogen.

Second: A method for evaluating the active oxygen scavengeability in water of dissolved hydrogen, which comprises a step of forcibly dissolving hydrogen in water without making a photosensitizing dye contained therein to thereby make the dissolved oxygen amount in water reach a predetermined initial concentration, followed by measuring the temporal dissolved oxygen amount in water, a step of forcibly dissolving hydrogen in water with making a photosensitizing dye contained therein to thereby adjust the dissolved oxygen amount in water to the initial concentration, followed by measuring the temporal dissolved oxygen amount in water with irradiation with light that contains the excitation wavelength for the photosensitizing dye, and a step of quantitatively evaluating the reaction between the dissolved hydrogen and the active oxygen based on the time-profile of the difference between the dissolved oxygen amount measured with making the photosensitizing dye contained in water and the dissolved oxygen amount measured without making the photosensitizing dye contained in water.

The inventors have investigated the active oxygen scavengeability of dissolved hydrogen water through ESR or fluorimetry, but could not obtain a good result. The inventors have found that the reason would be because the life of the experimentally generated active oxygen (singlet oxygen, hydrogen peroxide, superoxide anion radical, hydroxy radical, etc.) is short and the reaction thereof with a spin trapping agent (DMPO, TMPD, etc.) or a fluorescent reagent is extremely rapid, and therefore the quenching effect of hydrogen could not be observed.

Accordingly, the inventors have constructed an in-vitro evaluation system for directly observing the reaction between dissolved hydrogen and dissolved oxygen or dissolved active oxygen, and tested it and, as a result, have found that the system could make it possible to quantitatively evaluate the reaction speed and others, and have completed the present invention.

Advantage of the Invention

According to the invention, there is provided a novel technical means for obtaining useful knowledge in practical application of the antioxidant action of dissolved hydrogen, and practical application of active oxygen scavenging reaction in water.

BEST MODE FOR CARRYING OUT THE INVENTION

The invention is characterized by the above, and its embodiments are described below.

In the invention, water in which hydrogen is dissolved may be real water, but in accordance with the object for practical application to be the premise for evaluation of active hydrogen scavengeability or the like, an acid such as an amino acid, as well as a base, a salt or the like may be added thereto.

The evaluation system with water may be open to the atmosphere in accordance with the intended object, but may be closed from the atmosphere. In case where the system is open to the atmosphere, the equilibrium of oxygen under the atmospheric pressure and the dissolved oxygen in water must be taken into consideration in evaluating the measured results.

In the evaluation method for the reaction between the dissolved hydrogen and the dissolved oxygen in the invention, the dissolved oxygen amount in water is forcibly reduced by blowing thereinto any other gas than hydrogen to thereby make the dissolved oxygen amount in water reach a predetermined initial concentration, and then the temporal dissolved oxygen amount in water is measured. The other gas than hydrogen to be blown into water is, for example, an inert gas such as nitrogen or the like. Accordingly, the dissolved oxygen amount is reduced from the ordinary dissolution amount thereof at room temperature, from 7 to 8 ppm, to a level of from 1 to 5 ppm, thereby to reach the predetermined initial concentration.

For measuring the dissolved oxygen amount, a commercially-available dissolved oxygen analyzer can be used. The concentration profile data are plotted within a period of around 1 hour just after the dissolved oxygen amount has reached the predetermined initial concentration, whereby the change of the dissolved oxygen amount can be observed. For example, in measurement in a system open to the atmosphere, a linear dissolved oxygen amount increase owing to oxygen dissolution from the atmosphere into air can be observed.

In the invention, after the dissolved oxygen amount in water is adjusted to the initial concentration by forcibly dissolving hydrogen in water, the temporal dissolved oxygen amount in water is measured. For dissolving hydrogen in water, there may be employed a method of blowing gaseous hydrogen in water by bubbling; and apart from this, also employable is a microbubbles producing apparatus from which microbubbles of gaseous hydrogen may be blown into water and dispersed therein.

In that manner, hydrogen is dissolved in water until, as one example, the dissolved hydrogen concentration could be from 1 to 1.5 ppm or so. Accordingly, the dissolved oxygen amount could decrease from the ordinary dissolution amount, from 7 to 8 ppm, to a level of from 1 to 5 ppm, and the dissolved oxygen amount in water could be adjusted to the above-mentioned initial concentration.

The concentration profile data within a period of around 1 hour immediately after hydrogen dissolution are plotted, whereby the reduction in the dissolved oxygen amount caused by the $H_2O$ formation reaction between the dissolved hydrogen and the dissolved oxygen could be clarified.

With that, the reaction between the dissolved hydrogen and the dissolved oxygen is quantitatively evaluated based on the temporal profile of the difference between the dissolved oxygen amount measured with forcibly dissolving hydrogen and the dissolved oxygen amount measured with blowing the other gas than hydrogen. The quantitative evaluation includes stoichiometric analysis, reaction speed analysis, etc. So far as the present inventors know, there is no report relating to the profile change of the dissolved oxygen amount and the dissolved hydrogen amount as in Examples; and the invention provides a novel knowledge from the stoichiometric and macroscopic viewpoint relating to the reaction behavior between dissolved hydrogen and dissolved oxygen.

On the other hand, in the evaluation method for the active oxygen scavengeability in water of dissolved hydrogen in the invention, after the dissolved oxygen amount is made to reach a predetermined initial concentration by forcibly dissolving hydrogen in water without making a photosensitizing dye contained therein, and then the temporal dissolved oxygen amount in water is measured. The hydrogen dissolution and the dissolved oxygen amount measurement may be attained in the same manner as above.

With that, a photosensitizing dye is contained in water and hydrogen is forcibly dissolved therein to thereby adjust the dissolved oxygen amount in water to the above-mentioned initial concentration, and then with irradiation with light that contains the excitation wavelength for the photosensitizing dye, the temporal dissolved oxygen amount in water is measured. The photosensitizing dye includes methylene blue, rose Bengal or the like capable of promoting the formation of singlet oxygen.

As one example, hydrogen is dissolved in water until the dissolved hydrogen concentration could reach from 1 to 1.5 ppm or so, and accordingly, the dissolved oxygen amount is reduced from the ordinary dissolution amount at room temperature, from 7 to 8 ppm, to a level of from 1 to 5 ppm, whereby the dissolved oxygen amount in water can be adjusted to the above-mentioned initial concentration.

The concentration profile data within a period of around 1 hour immediately after hydrogen dissolution are plotted, whereby the reduction in the dissolved oxygen amount caused by the $H_2O$ formation reaction between the dissolved hydrogen and the dissolved oxygen could be clarified.

With that, the reaction between the dissolved hydrogen and the dissolved oxygen is quantitatively evaluated based on the temporal profile of the difference between the dissolved oxygen amount measured with making the photosensitizing dye contained in water and the dissolved oxygen amount measured without making the photosensitizing dye contained in water. The quantitative evaluation includes stoichiometric analysis, reaction speed analysis, etc. So far as the present inventors know, there is no report relating to the profile change of the dissolved oxygen amount and the dissolved hydrogen amount as in Examples; and the invention provides a novel knowledge from the stoichiometric and macroscopic viewpoint relating to the reaction behavior between dissolved hydrogen and dissolved oxygen.

The invention is favorably usable in collecting basic data and the like in various fields of medicine, industry, agriculture, food, environment and others.

EXAMPLES

The invention is described in more detail with reference to the following Examples; however, the invention should not be limited at all by these Examples.

Example 1

500 ml of distilled water, as a sample, was put into a 500-ml glass bottle having a diameter of 8 cm and a height of 11 cm with its top face kept open to the atmosphere, and with stirring and using a dissolved hydrogen meter and a dissolved oxygen meter, the dissolved hydrogen amount and the dissolved oxygen amount were measured under various experimental conditions. The dissolved hydrogen amount and the dissolved oxygen amount were determined just before the start of the experiment, and the temporal change thereof after that was measured; and after 30 minutes, platinum black was added and the measurement was further continued.

As the dissolved hydrogen meter, used was Kyoei Electronic Laboratory's KM2100 DH; and as the dissolved oxygen meter, used was HORIBA DO METER OM-51.

The water sample was bubbled with hydrogen gas, and the test start condition of the dissolved oxygen amount in the sample, 0.953 mm, and the dissolved oxygen amount therein, 2.92 ppm were determined. After that, the temporal change of the dissolved oxygen amount and that of the dissolved oxygen amount were measured and the data are shown in FIG. 1 and FIG. 2 (no addition of methylene blue, irradiation with fluorescent lamp).

The dissolved oxygen amount in equilibrium with air was 8.3 ppm; but with hydrogen gas bubbling, the dissolved oxygen was expelled and reduced to 2.92 ppm.

Figure 1:
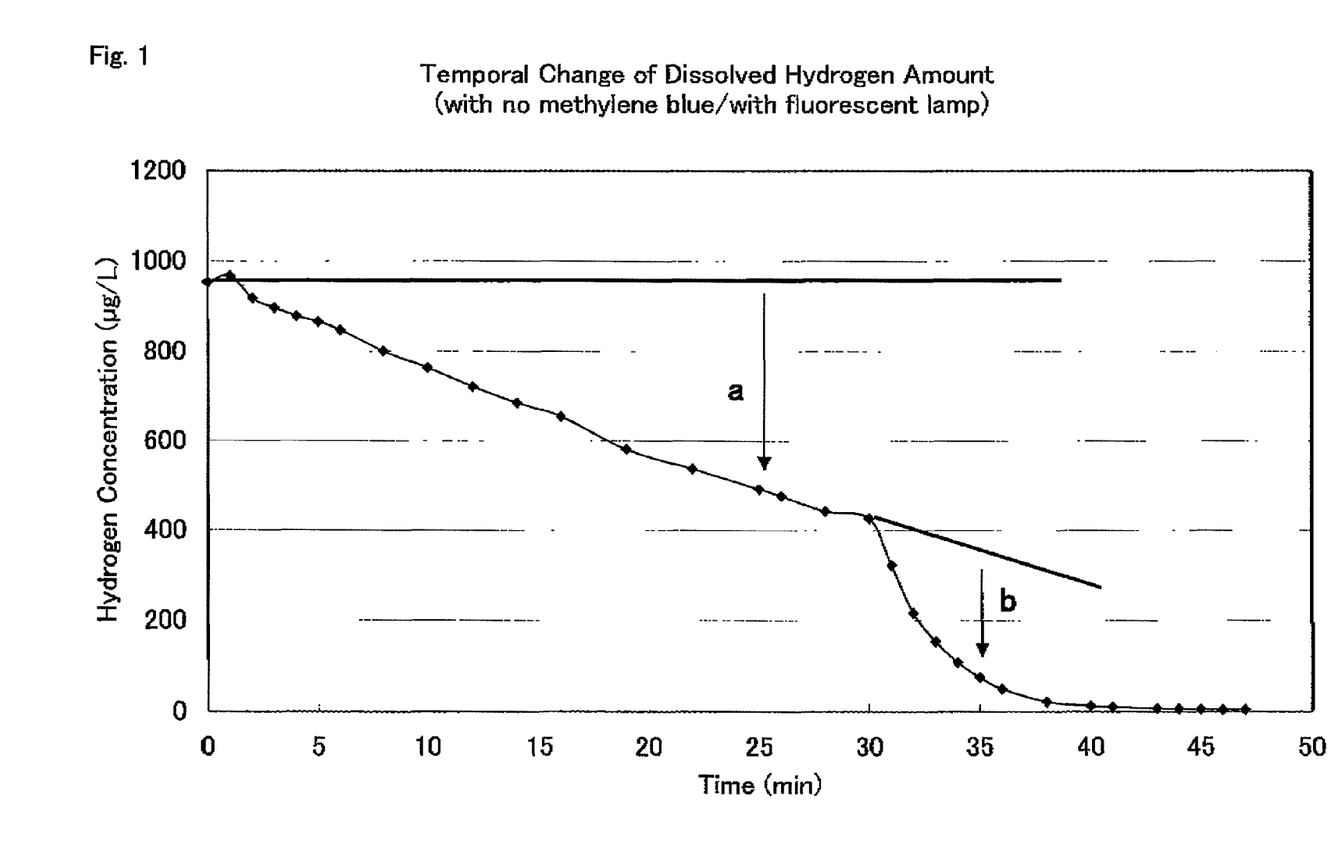
FIG. 1 is a graph showing the temporal change of the dissolved hydrogen amount in Example 1.
Figure 2:
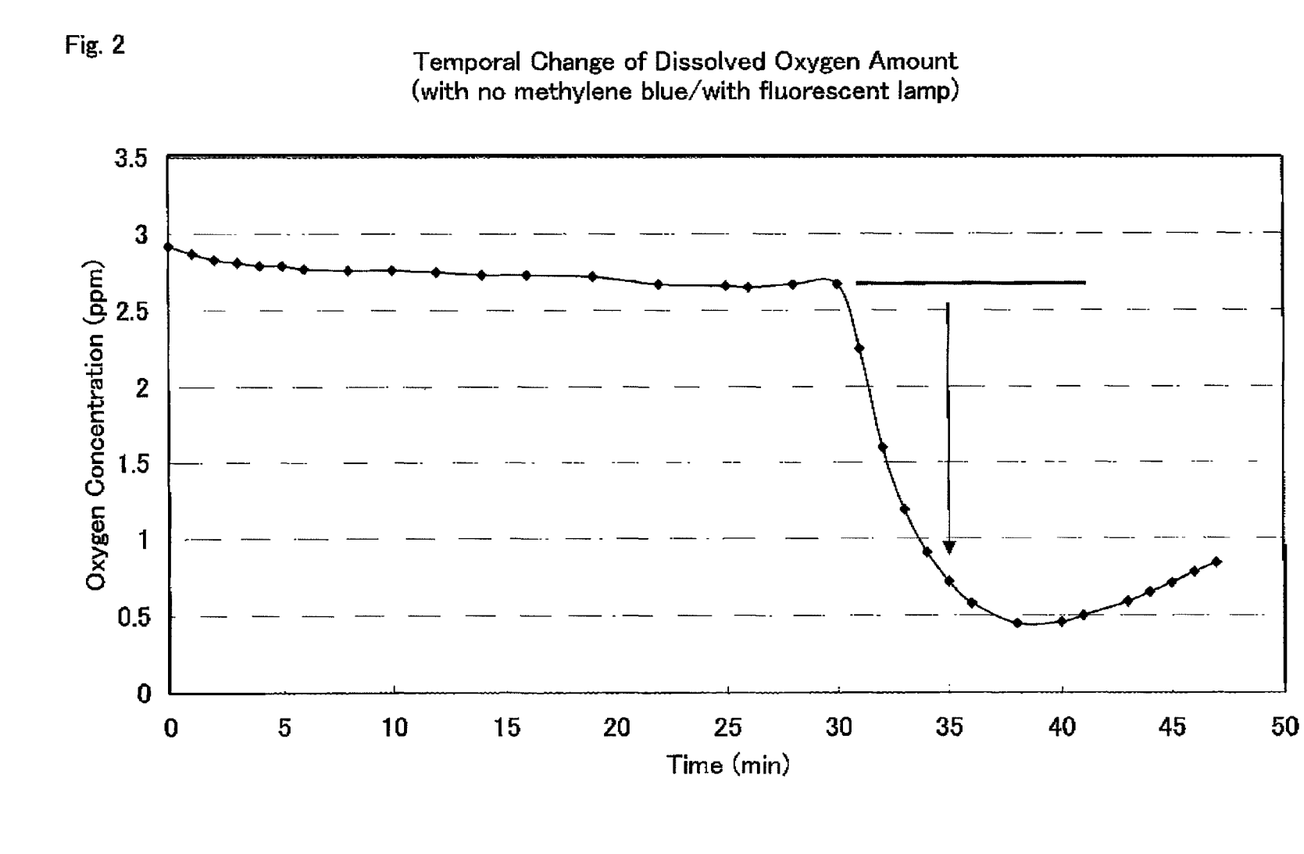
FIG. 2 is a graph showing the temporal change of the dissolved oxygen amount in Example 1.

As in FIG. 1, the dissolved hydrogen amount linearly decreased from 0.953 ppm, and after 30 minutes, it reached 0.427 ppm. It is understood that the dissolved hydrogen decrease (arrow a) would be determined by the balance between the reaction amount of the dissolved hydrogen with the dissolved oxygen and the amount of the hydrogen gas release to air.

On the other hand, when platinum black (about 5 mg) was added after 30 minutes, then the dissolved hydrogen drastically decreased, and in 10 minutes after the addition, it reached zero. It is understood that the drastic reduction in the dissolved hydrogen would be because the dissolved hydrogen could be activated by the platinum catalyst and the reaction speed thereof with the dissolved oxygen would increase. The net decrease in the dissolved hydrogen amount (arrow b) induced by the platinum catalyst addition was computed to be 0.260 ppm/5 min.

On the other hand, regarding the temporal change of the dissolved oxygen amount, the amount was almost constant with no change in 30 minutes after the start of the experiment, as shown in FIG. 2; but when platinum black (about 5 mg) was added after 30 minutes, then the amount drastically decreased, and after 8 minutes, it reached the lowest value of 0.45 ppm, and thereafter it gradually increased.

The dissolved oxygen amount did not almost change in 30 minutes after the start of the experiment, and the result would be because the reduction in the oxygen amount owing to the reaction between the dissolved oxygen and the dissolved hydrogen could be balanced with the oxygen amount dissolved and replenished from air. Accordingly, after the platinum catalyst addition, the dissolved oxygen amount decreased owing to the reaction between the activated dissolved hydrogen and the dissolved oxygen, and the decrease (arrow) was computed to be 1.85 ppm/5 min. The molar ratio of the net decrease in the dissolved hydrogen to that of the dissolved oxygen after reaction with the platinum catalyst addition could be about 2/1, and therefore, it is understood that the above results could support the reaction between the dissolved hydrogen and the dissolved oxygen.

Figure 3:
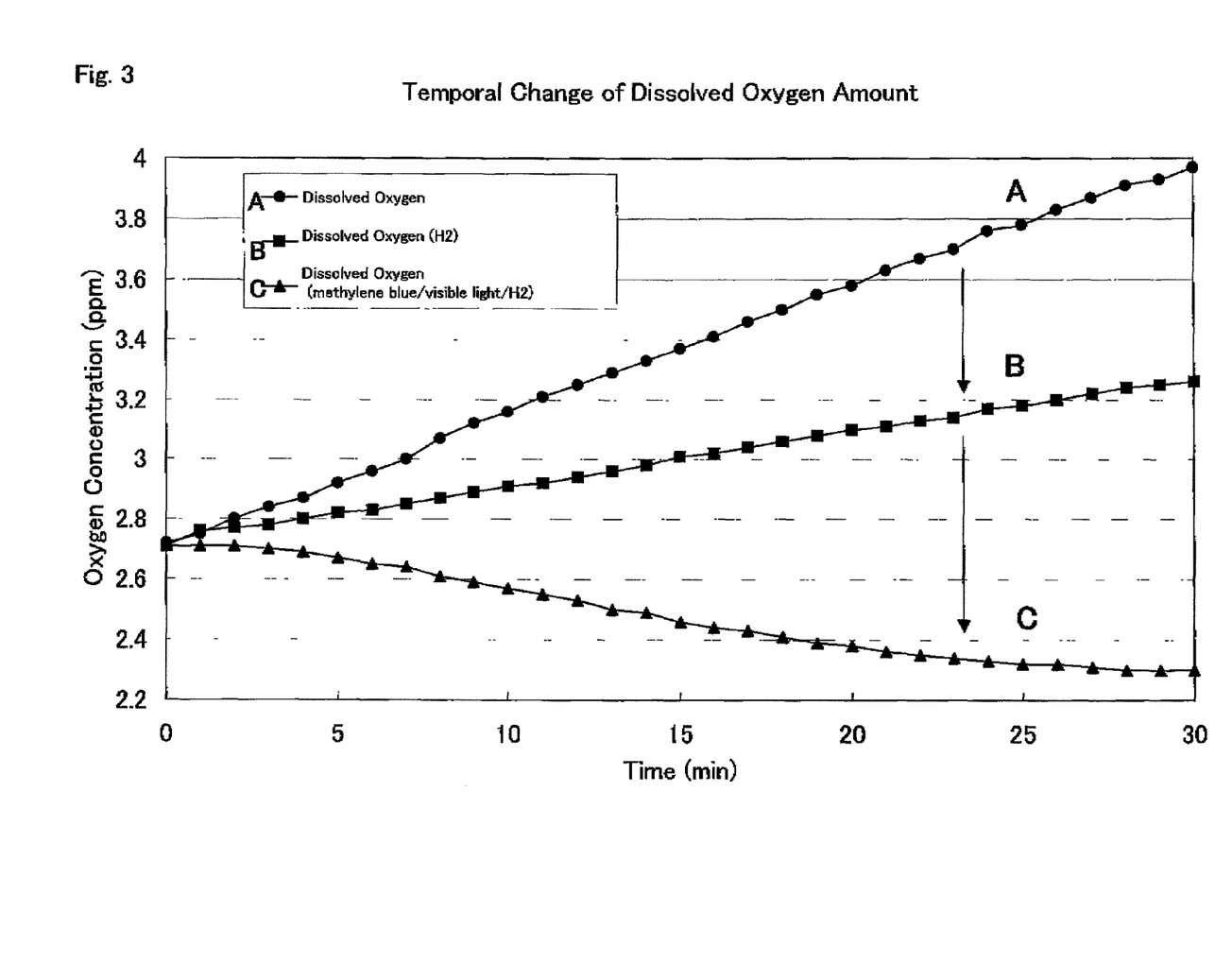
FIG. 3 is a graph showing the temporal change of the dissolved oxygen amount (with $N_2$ bubbling, $H_2$ bubbling, methylene blue and light irradiation+$H_2$ bubbling) in Example 1.
Figure 4:
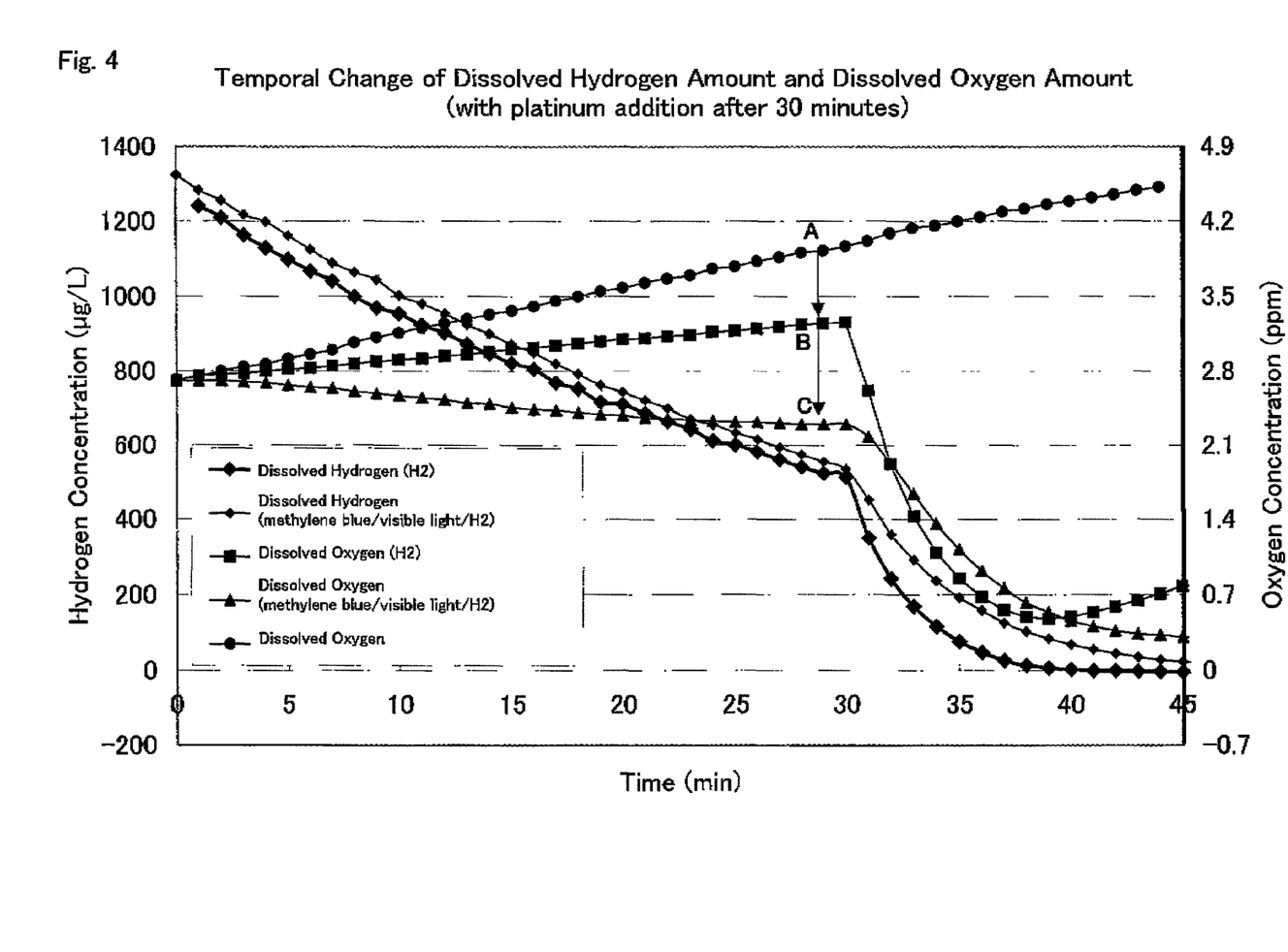
FIG. 4 is a graph showing the temporal change of the dissolved hydrogen amount and the dissolved oxygen amount in Example 1.

Next, a photosensitizing dye, methylene blue was used in the experiment, and the results are shown in FIG. 3 and FIG. 4. In FIG. 3, the line A indicates the data of the temporal change of the sample, in which the initial concentration of the dissolved oxygen was controlled to be about 2.7 ppm through nitrogen gas bubbling. The line B indicates the data of the temporal change of the sample, in which the initial concentration of the dissolved oxygen was controlled to be about 2.7 ppm through hydrogen gas bubbling. The line C indicates the data of the temporal change of the sample, in which the initial concentration of the dissolved oxygen was controlled to be about 2.7 ppm through hydrogen gas bubbling; and in this, a photosensitizing dye methylene blue (2 mM) was dissolved in 500 ml of the water sample, and the temporal change of the dissolved oxygen was measured with continuous irradiation (including $\lambda=670$ nm) with incandescent light (500 W) at a distance of 30 cm from the sample. FIG. 4 shows the temporal change of the dissolved hydrogen concentration and the dissolved oxygen concentration with addition of platinum black after 30 minutes.

In FIG. 3, the linear increase in the dissolved oxygen represented by the line A indicates the increase in the oxygen amount dissolved and replenished from air. The line B of the sample containing dissolved oxygen is determined by the balance between the reduction in the dissolved oxygen caused by the reaction of hydrogen and oxygen, and the increase in the oxygen amount dissolved and replenished from air. Accordingly, the difference between the line A and the line B suggests the decrease in the dissolved oxygen owing to the reaction between the dissolved hydrogen and the dissolved oxygen.

The reduction in the dissolved oxygen represented by the line C is supported by the balance between the increase in the oxygen amount dissolved and replenished from air, the decrease in the dissolved oxygen owing to the reaction of hydrogen and oxygen, and the decrease owing to the reaction of dissolved hydrogen and active oxygen (singlet oxygen). In this, the active oxygen (singlet oxygen) is generated through light irradiation (including $\lambda$=670 nm) of the photosensitizing dye methylene blue.

From the above results, the difference between the line B and the line C suggests the decrease in the dissolved oxygen owing to the reaction between the dissolved hydrogen and the active oxygen (singlet oxygen).

Figure 5:
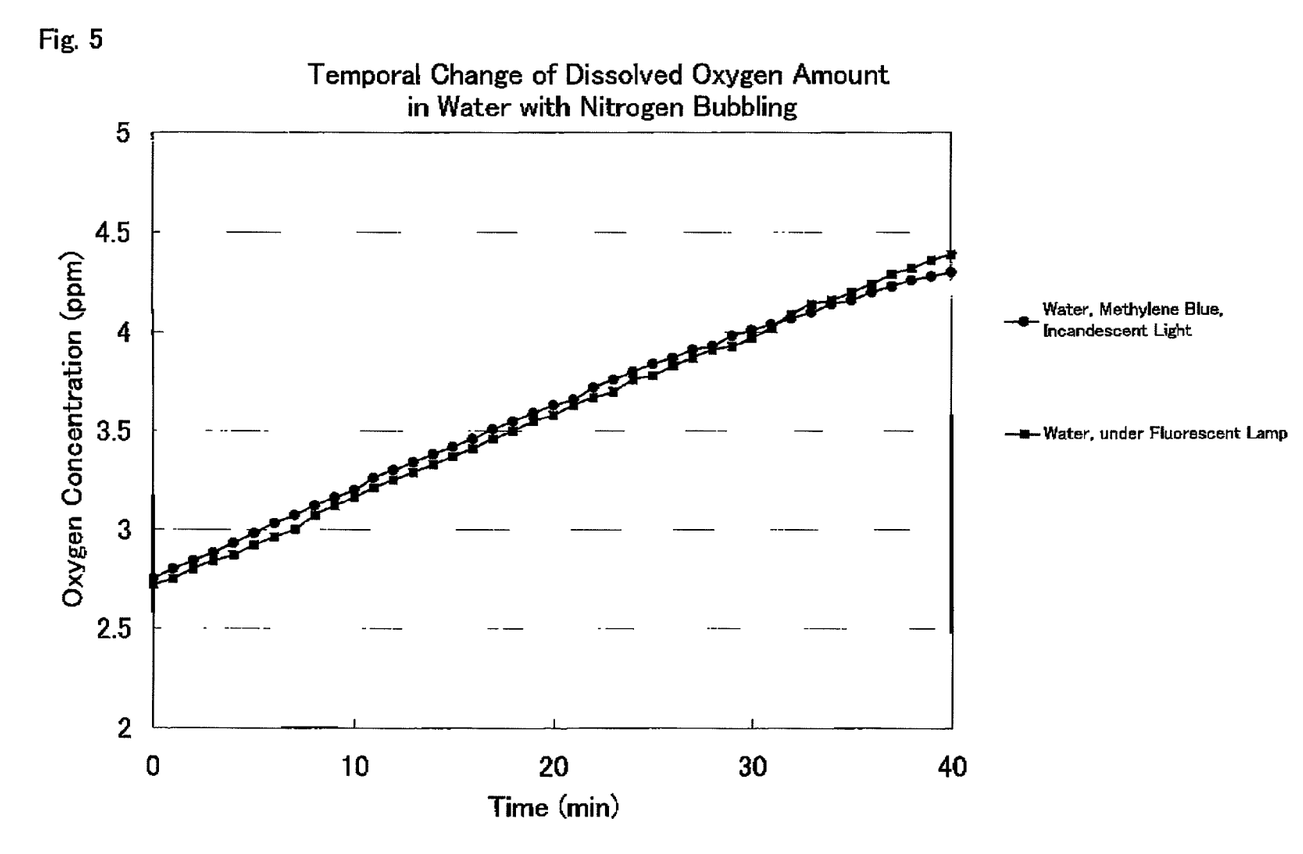
FIG. 5 is a graph showing the temporal change of the dissolved oxygen amount in a sample with nitrogen gas bubbling therein, as compared with each other in point of the presence or absence of methylene blue dissolution and incandescent light irradiation.

FIG. 5 shows the result of the temporal change for 40 minutes of the dissolved oxygen amount controlled to be 2.7 ppm in a sample with nitrogen gas bubbling therein in FIG. 3, and the result of the temporal change of the dissolved oxygen amount controlled to be 2.7 ppm in a sample of an aqueous solution of methylene blue dissolved therein, with nitrogen gas bubbling therein and with irradiation with incandescent light. To both the two, platinum black was added after 30 minutes; however, no influence of the platinum catalyst appeared at all on the two. The two lines are nearly the same, from which it is obvious that no influence of the platinum catalyst appears on the cases where dissolved hydrogen does not exist, and that the presence or absence of methylene blue and the presence or absence of incandescent light irradiation have no influence on the change in the dissolved oxygen amount.

Based on the above results, further investigations were made relating to the reaction speed between the dissolved hydrogen and the dissolved oxygen in water and the reaction speed between the dissolved hydrogen and the active oxygen.

The reaction speed $V_{O2}$ in antioxidant reaction is represented by the following formula:

$$V_{O2}=-d[O_2]/dt=k_1[O_2]^n$$

On the other hand, the reaction speed $V_{O2*}$ in active oxygen scavenging is represented by the following formula:

$$V_{O2*}=-d[O_2]/dt=k_1[O_2*]^n$$

From the results in FIG. 1 to FIG. 4 (and from the results in Example 2 give hereinunder), the relation of time vs concentration ($O_2$, $O_2*$, $H_2$) is all a linear relationship. This suggests that the reaction speed is a constant value k irrespective of time. In other words, it may be considered that the reaction is a 0-order reaction.

With that, the concrete data of the reaction speed $V_{O2}$, $V_{O2*}$ were computed from the experimental data in FIG. 3. The decrease in the dissolved oxygen owing to the reaction between dissolved hydrogen and dissolved oxygen after 30 minutes is (A−B)=4−3.25=0.75 ppm/30 min. Accordingly, $V_{O2}$ could be estimated as $V_{O2}=-d[O_2]/dt=(0.75/32)$ mM/30 min=0.78 $\mu$Mmin$^{-1}$=$k_1$.

The decrease in the active oxygen owing to the reaction between dissolved hydrogen and active oxygen after 30 minutes is (B−C)=3.15−2.3=−0.95 ppm/30 min. Accordingly, $V_{O2*}$ could be estimated as $V_{O2*}=-d[O_2*]/dt=(0.95/32)$ mM/30 min=0.99 $\mu$Mmin$^{-1}$=$k_2$.

The above results are the reaction speed and the reaction speed constant at 25° C.; however, when the activation energy is estimated from the Arrhenius formula on the assumption of the case of measurement in changing the temperature, the activation energy for the reaction of $2H_2+O_2 \rightarrow 2H_2O$ in the solution state is presumed to be on the order of 7 kJmol$^{-1}$. The activation energy for the reaction of $2H_2+O_2* \rightarrow 2H_2O$ in the solution state is presumed to be on the order of 6 KJmol$^{-1}$.

Example 2

Figure 6:
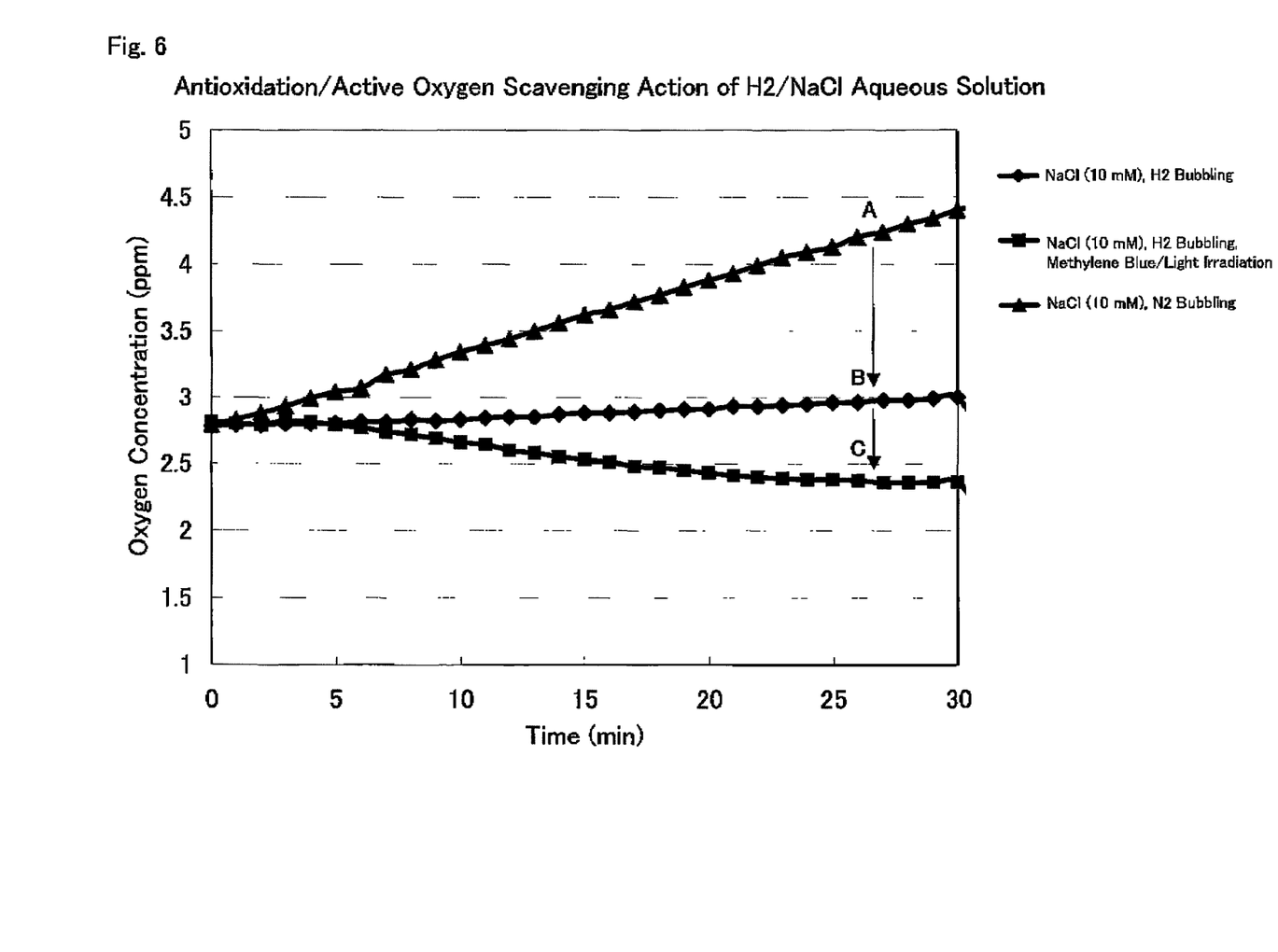
FIG. 6 is a graph showing the temporal change of the dissolved oxygen amount in Example 2 ($H_2$/NaCl aqueous solution).
Figure 7:
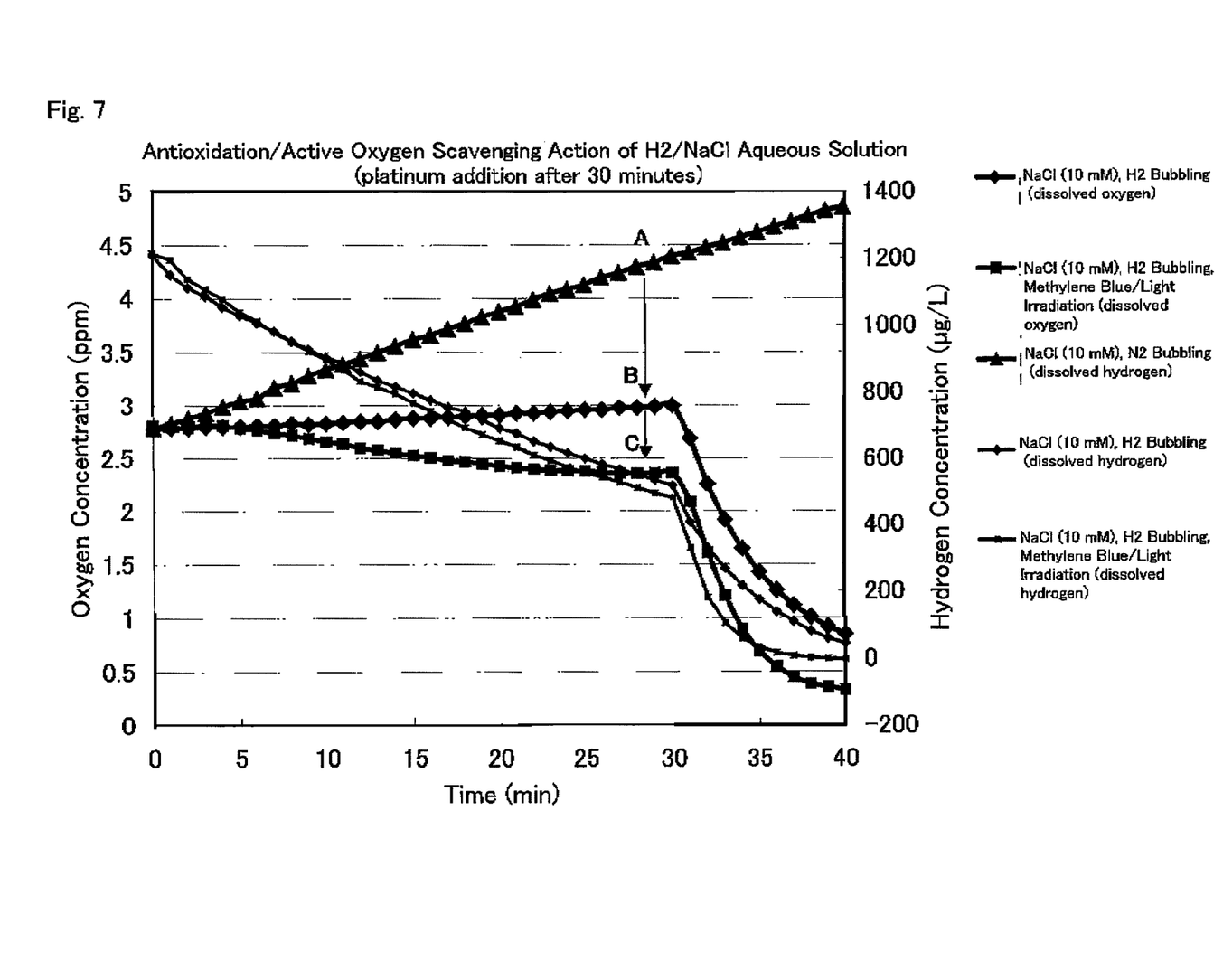
FIG. 7 is a graph showing the temporal change of the dissolved hydrogen amount and the dissolved oxygen amount in Example 2 ($H_2$/NaCl aqueous solution).
Figure 8:
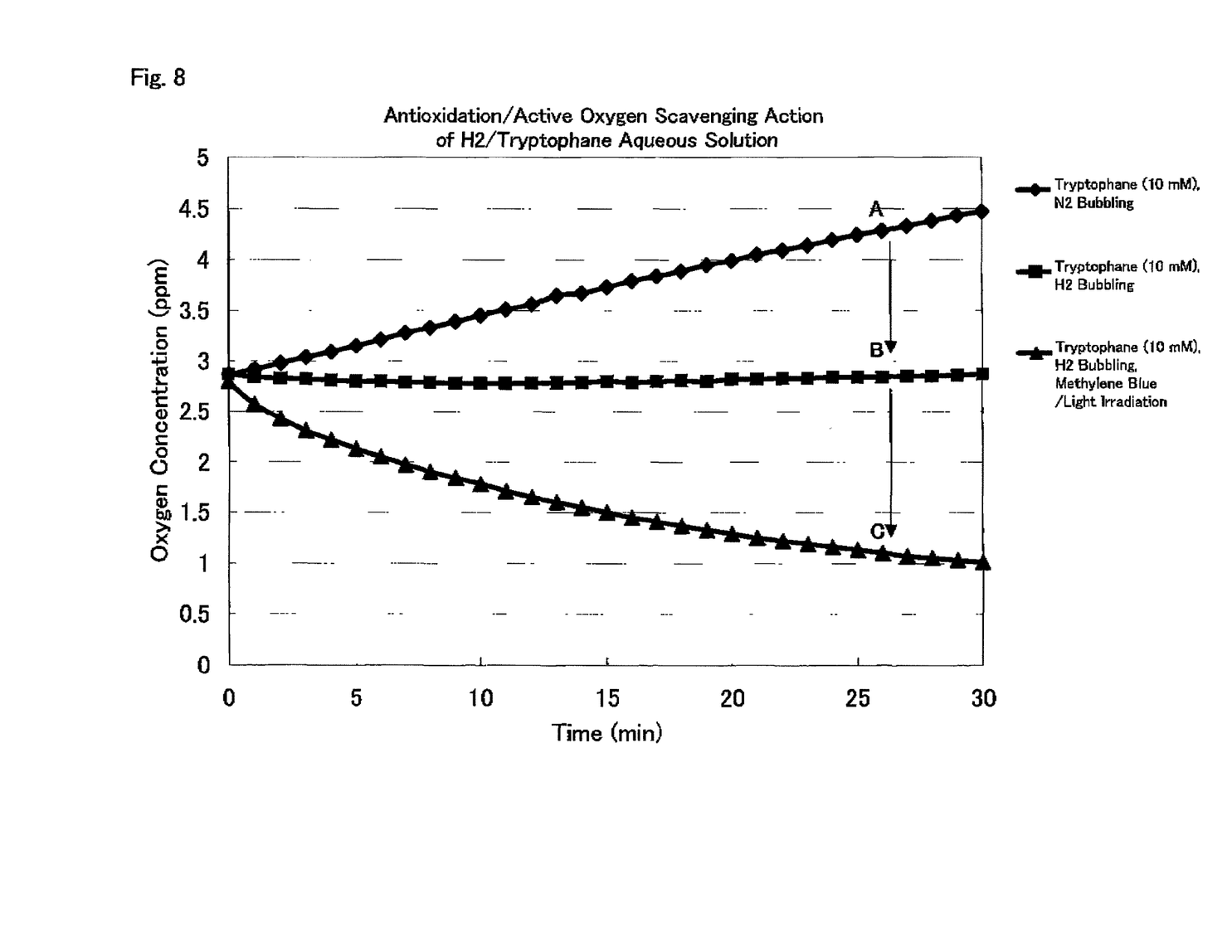
FIG. 8 is a graph showing the temporal change of the dissolved oxygen amount in Example 2 ($H_2$/tryptophane aqueous solution).
Figure 9:
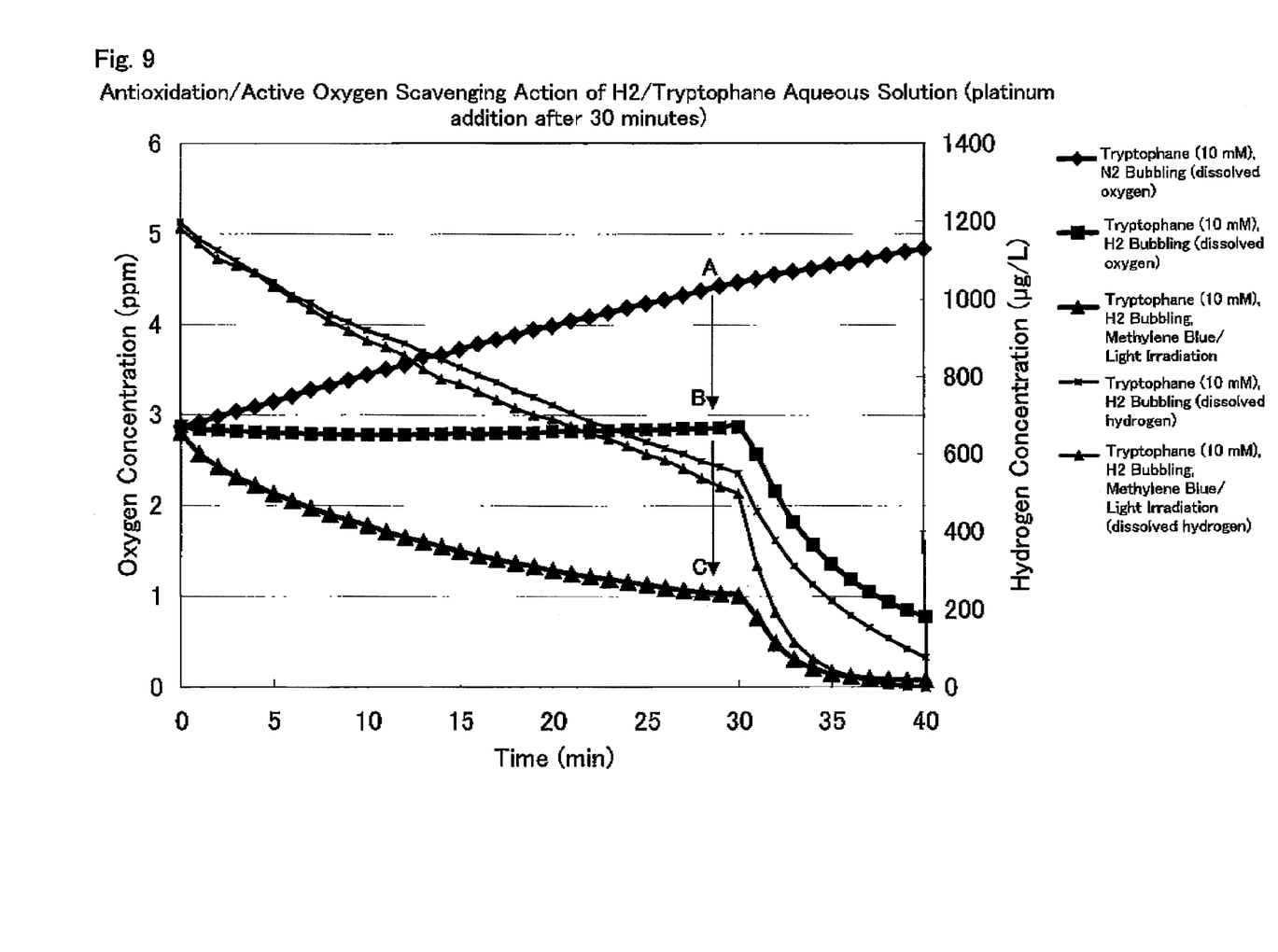
FIG. 9 is a graph showing the temporal change of the dissolved hydrogen amount and the dissolved oxygen amount in Example 2 ($H_2$/tryptophane aqueous solution).
Figure 10:
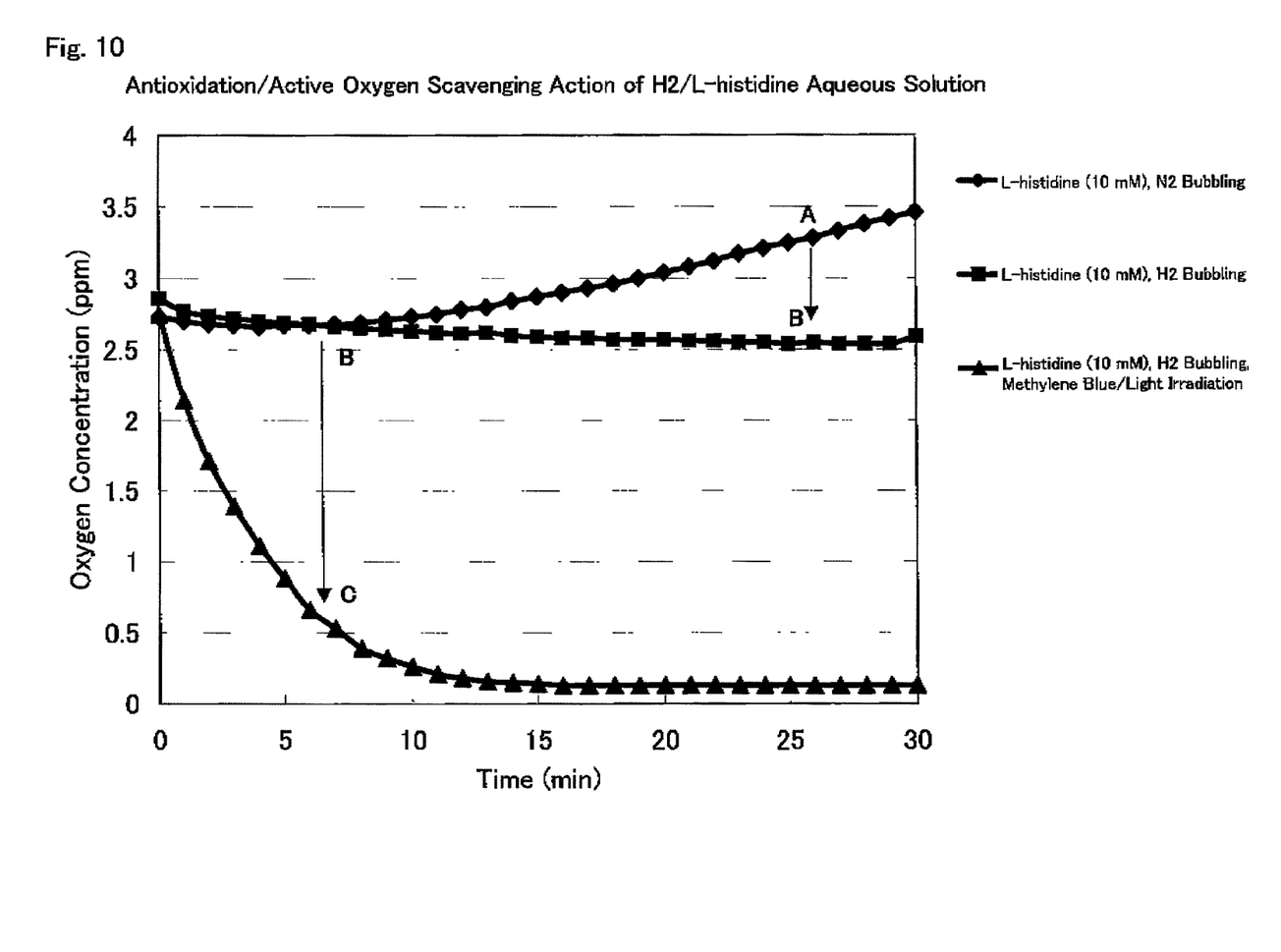
FIG. 10 is a graph showing the temporal change of the dissolved oxygen amount in Example 2 ($H_2$/L-histidine aqueous solution).
Figure 11:
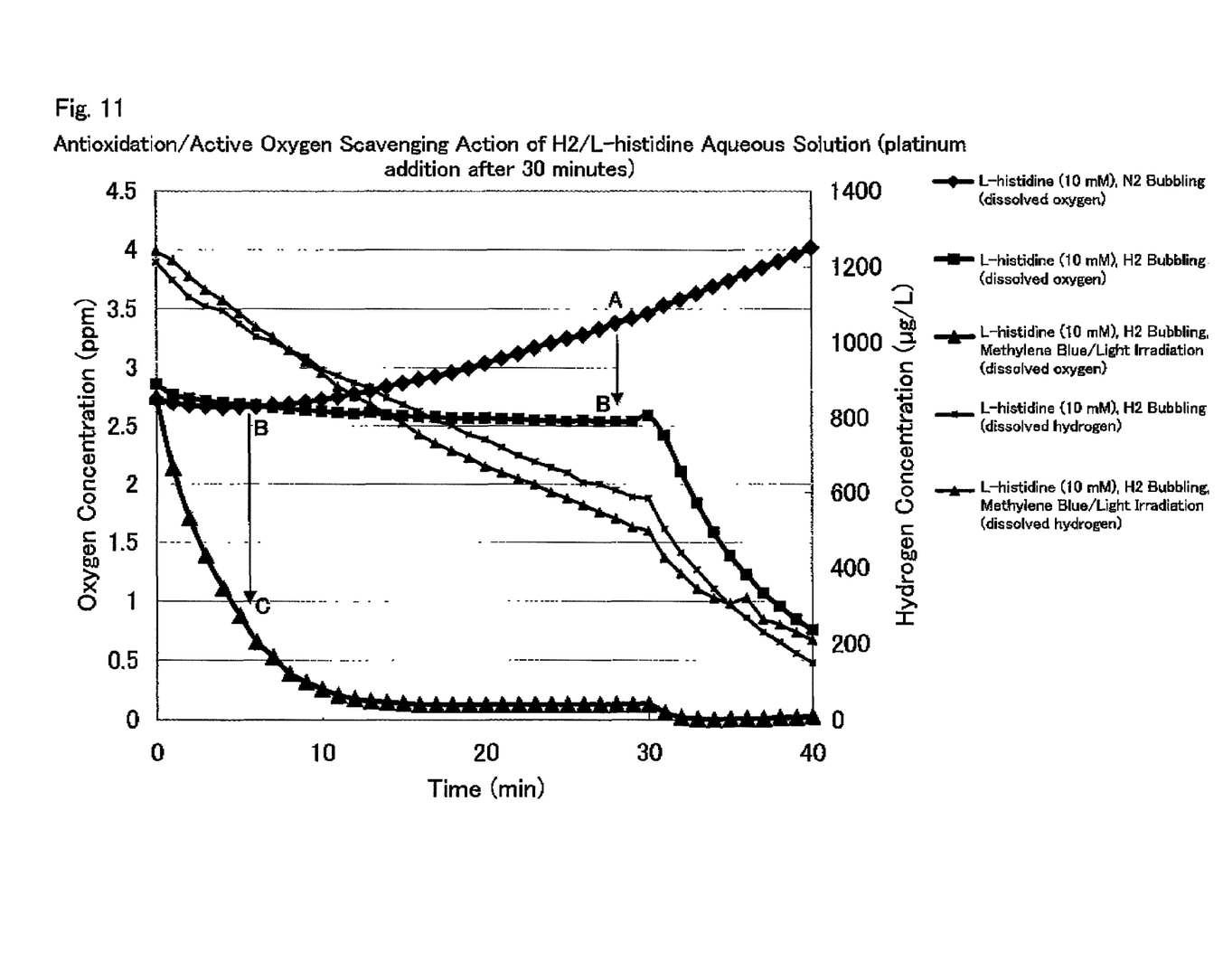
FIG. 11 is a graph showing the temporal change of the dissolved hydrogen amount and the dissolved oxygen amount in Example 2 ($H_2$/L-histidine aqueous solution).

As aqueous solution samples, used were 10 mM NaCl aqueous solution (FIG. 6, FIG. 7), 10 mM tryptophane aqueous solution (FIG. 8, FIG. 9) and 10 mM L-histidine aqueous solution (FIG. 10, FIG. 11). The others were the same as in FIG. 3 and FIG. 4 in Example 2. The temporal change of the dissolved oxygen concentration in cases of $N_2$ bubbling, $H_2$ bubbling, methylene blue and light irradiation+$H_2$ bubbling (FIG. 6, FIG. 8, FIG. 10); and the temporal change of the dissolved hydrogen concentration and the dissolved oxygen concentration with platinum black addition after 30 minutes (FIG. 7, FIG. 9, FIG. 11) were measured. The temporal change of the dissolved hydrogen amount and the dissolved oxygen amount was monotonous decrease or monotonous increase, and its tendency was the same as in Example 1. From this result, it is presumed that the reaction between dissolved hydrogen and dissolved oxygen and the reaction between dissolved hydrogen and active oxygen would be both at a 0-order chemical reaction speed.

The above results clarified that, according to the in-vitro experimental method, dissolved hydrogen and dissolved oxygen, and dissolved hydrogen and active oxygen could react under the experimental condition of a ppm-order concentration and a ten-minute timescale reaction speed. It has been clarified that, from the difference between A and B in the drawings, $2H_2+O_2 \rightarrow 2H_2O$, or that is, the antioxidation reaction (antioxidation action of dissolved hydrogen) can be quantitatively evaluated; and on the other hand, from the difference between B and C, $2H_2+O_2* \rightarrow 2H_2O$, or that is, the active oxygen scavenging reaction (active oxygen (singlet oxygen $O_2*$) scavenging action of dissolved hydrogen) can be quantitatively evaluated.

The invention claimed is:

1. A method for evaluating the reaction between dissolved hydrogen and dissolved oxygen, which comprises a step of forcibly reducing the dissolved oxygen amount in water by blowing thereinto any other gas than hydrogen to thereby make the dissolved oxygen amount in water reach a predetermined initial concentration, followed by measuring the temporal dissolved oxygen amount in water, a step of forcibly dissolving hydrogen in water to thereby adjust the dissolved oxygen amount in water to the initial concentration, followed by measuring the temporal dissolved oxygen amount in water, and a step of quantitatively evaluating the reaction between the dissolved hydrogen and the dissolved oxygen based on the time-profile of the difference between the dissolved oxygen amount measured with forcibly dissolving hydrogen and the dissolved oxygen amount measured with blowing the other gas than hydrogen.

2. A method for evaluating the active oxygen scavengeability in water of dissolved hydrogen, which comprises a step of forcibly dissolving hydrogen in water without making a photosensitizing dye contained therein to thereby make the dissolved oxygen amount in water reach a predetermined initial concentration, followed by measuring the temporal dissolved oxygen amount in water, a step of forcibly dissolving hydrogen in water with making a photosensitizing dye contained therein to thereby adjust the dissolved oxygen amount in water to the initial concentration, followed by measuring the temporal dissolved oxygen amount in water with irradiation with light that contains the excitation wavelength for the photosensitizing dye, and a step of quantitatively evaluating the reaction between the dissolved hydrogen and the active oxygen based on the time-profile of the difference between the dissolved oxygen amount measured with making the photosensitizing dye contained in water and the dissolved oxygen amount measured without making the photosensitizing dye contained in water.

* * * * *